(12) United States Patent
Keijsper et al.

(10) Patent No.: US 6,307,095 B1
(45) Date of Patent: Oct. 23, 2001

(54) PROCESS FOR THE PREPARATION OF VINYLESTERS

(76) Inventors: Johannes Jacobus Keijsper; Jean-Paul Lange, both of Badhuisweg 3, 1031 CM Amsterdam (NL); Brendan Dermot Murray, 1118 Stoneyhill Dr., Houston, TX (US) 77077

( * ) Notice: Subject to any disclaimer, the term of this patent is extended or adjusted under 35 U.S.C. 154(b) by 0 days.

(21) Appl. No.: 08/950,427

(22) Filed: Oct. 15, 1997

(30) Foreign Application Priority Data

Oct. 15, 1996 (EP) .................................................. 96202874

(51) Int. Cl.$^7$ .................................................. C07C 67/04
(52) U.S. Cl. .............................................................. 560/242
(58) Field of Search .............................................. 560/242

(56) References Cited

U.S. PATENT DOCUMENTS

| | | | |
|---|---|---|---|
| 3,285,941 | 11/1966 | Engel et al. | 260/410.9 |
| 3,287,402 | 11/1966 | Landis | 260/498 |
| 3,607,915 | 9/1971 | Borsboom et al. | 260/498 |
| 3,634,496 | 1/1972 | Kominami et al. | 260/497 A |
| 4,488,996 | 12/1984 | Serota | 260/410.9 R |

FOREIGN PATENT DOCUMENTS

| | | |
|---|---|---|
| 1206400 | 4/1963 | (DE) . |
| 3030044 | 3/1982 | (DE) .............................. C07C/67/04 |

*Primary Examiner*—Samuel Barts

(57) ABSTRACT

A process for the catalytic conversion of carboxylic acids with acetylene to vinylesters.

At least one, preferably saturated, secondary carboxylic ester and/or at least one, preferably tertiary carboxylic acid is (are) passed in the gas phase together with acetylene at an elevated temperature, preferably in the range of from 150 to 400° C., over a catalyst comprising zinc and a solid inert oxidic carrier, preferably alumina.

The carboxylic acids have advantageously the following formula:

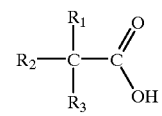

in which $R_1$ is H or an alkyl group and $R_2$ and $R_3$ are alkyl groups, the total number of C-atoms of $R_1+R_2+R_3$ being in the range of from 3 to 18.

These vinylesters have a good stability and are particularly useful components in emulsion paints and as modifiers in alkyd and epoxy resin.

16 Claims, No Drawings

PROCESS FOR THE PREPARATION OF VINYLESTERS

FIELD OF THE INVENTION

The present invention relates to a process for the catalytic conversion of carboxylic acids with acetylene to vinylesters.

BACKGROUND OF THE INVENTION

DE-A-3,030,044 describes the catalytic reaction of acetylene with primary carboxylic acids, such as acetic acid, propionic acid, butyric acid and formic acid, in the gas phase. The catalyst preferably contains zinc deposited on a solid inert carrier.

SUMMARY OF THE INVENTION

A process for the catalytic conversion of carboxylic acids with acetylene to vinylesters comprising the steps of passing over a catalyst comprising zinc and a solid inert oxidic carrier, at least one secondary carboxylic acid and/or at least one tertiary carboxylic acid in the gas phase together with acetylene at an elevated temperature.

DETAILED DESCRIPTION OF THE INVENTION

The present invention provides an efficient means to convert these branched carboxylic acids to vinylesters. Such branched vinylesters are expected to be prepared more difficulty than the vinylesters of the low boiling primary acids according to DE-A-3,030,044.

The invention therefore relates to a process for the catalytic conversion of carboxylic acids with acetylene to vinylesters, characterized in that at least one secondary carboxylic acid and/or at least one tertiary carboxylic acid is (are) passed in the gas phase together with acetylene at an elevated temperature over a catalyst comprising zinc and a solid inert oxidic carrier.

The vinylesters of the secondary and tertiary carboxylic acids have a good chemical stability and are particularly useful in polymeric and copolymeric compounds, such as emulsion paints and as modifiers in alkyd and epoxy resins.

While the present process is adaptable to a variety of starting materials in the secondary and/or tertiary carboxylic acids group, it is important to note that the operation of the process requires the carboxylic acids to be vaporized.

At temperatures above 400° C. all carboxylic acids experience decomposition and therefore the acids which can be vaporized at or under 400° C. are the most suitable starting materials for the preparations of the vinylesters by the present process, and the temperature of the process does preferably not exceed 400° C.

Generally, carboxylic acids having in excess of 20 carbon atoms are prone to thermally decompose prior to vaporization and therefore are not suitable starting materials for the process.

A very important group of carboxylic acids, which are suitable starting materials, is the group of carboxylic acids containing a tertiary or quaternary carbon atom in the alpha or beta position with respect to the carboxyl group, i.e. the saturated aliphatic monocarboxylic acids in which the carboxyl group is directly linked to the tertiary or quaternary carbon atom. Since these acids have branched chains their boiling points are generally lower than the isomeric unbranched acids of the series containing 20 or less carbon atoms per molecule. Therefore these alpha-branched acids are the preferred starting materials in the present process.

The preferred starting materials are saturated secondary and/or tertiary carboxylic acids having the following formula:

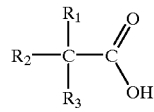

wherein $R_1$ is hydrogen or alkyl and $R_2$ and $R_3$ are alkyl groups, the total number of C-atoms of $R_1+R_2+R_3$ being within the range of from 3 to 18. A suitable example is 2-ethyl-hexanoic acid. The acids can be prepared by the reaction of $C_{3-18}$ olefinic hydrocarbon fraction with formic acid or alternatively with carbon monoxide and water in an acid catalyzed reaction.

Since this acid generally has a boiling point above 150° C., dependent on its partial pressure in the gaseous reaction mixture, the minimum temperature of the present process is preferably 150° C.

While the molar ratio of the acetylene to the vaporized carboxylic acid(s) in the gaseous mixture to be converted to vinylesters can vary within broad limits, the preferred range is from 0.5 to 10, more preferably from 1 to 5.

Ratios outside the preferred limits can be used but with a sacrifice in the yield.

Good conversion of the vaporized carboxylic acids with acetylene to the vinylesters are obtained if the reaction is performed at atmospheric pressure, although lower and higher pressures are possible. The reaction is preferably carried out at a pressure in the range of from 0.1 to 5.0 bar.

Advantageously the pressure does not exceed 24 bar, because the application of pressures substantially above this value necessitates the use of special apparatus with safety measures to eliminate any risk of explosion.

The present reaction is suitably carried out in a continuous way. In order to warrant a sufficiently long residence time of the reactants in the reactor the weight hourly space velocity (WHSV) of the acid(s) is preferably in the range of from 0.2 to 10 grams acid(s) per gram catalyst per hour, more preferably 0.5 to 5 g/g/h, if the molar ratio between acetylene and acid(s) is maintained within the range which has been mentioned hereinbefore.

The catalyst comprises zinc and any solid inert oxidic carrier. Suitable carriers are silica, silica/alumina, titania, zirconia, magnesia, chromia, niobia, manganese oxide, vanadium oxide, the oxides of the lanthanides and the zeolites, and mixtures of these oxides.

The preferred catalyst carrier is alumina, because the best results were obtained with this support.

The catalyst is advantageously prepared by impregnating the solid inert oxidic carrier with a solution of at least one zinc salt, preferably zinc nitrate and/or zinc acetate, and by drying the impregnated carrier. If a zinc salt of an inorganic acid or of acetic acid is used, an aqueous solution of the zinc salt is applied for the impregnation. If alternatively an organic zinc salt is used, the carrier is suitably soaked with a solution of the zinc salt in an alcohol of an ether, followed by the evaporation of the solvent. The concentration of the zinc on the carrier may vary between wide limits, but zinc contents of the catalyst in the range of from 0.1 to 30% wt are preferred. In most cases zinc contents in the range of from 1 to 20% wt can advantageously be used.

The catalyst can be in any form, dependent on the way in which the present process is carried out, e.g. in a fixed bed, a fluid bed or a moving bed. For a fixed bed or a moving bed catalyst spheres, pellets or extrudates, having dimensions of 0.3 to 5 mm, are suitable. For a fluid bed, the catalyst is in the form of a powder.

Though we do not want to be bound by theory, it is assumed that the zinc is present on the carrier in the form of a zinc salt of the secondary or tertiary carboxylic acid that is to be converted with the acetylene to a vinylester of the general formula:

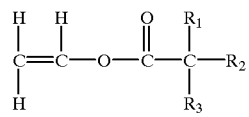

where R1, R2, R3 being as defined hereinbefore.

ILLUSTRATIVE EMBODIMENTS

The invention will now be illustrated by the following non-limiting examples.

EXAMPLE 1

A catalyst was prepared by impregnating an alumina support with a solution of zinc nitrate. After drying the finished catalyst contained 10% wt Zn.

A mixture of saturated tertiary carboxylic acids with 10 C-atoms per molecule and acetylene were passed over a fixed bed of this catalyst under the following conditions:

Temperature: 252° C.

WHSV: 0.714 g acid/g catalyst/h
:0.497 g acetylene/g catalyst/h

Pressure: 1 bar

Molar ratio acetylene/acids: 4.6

The conversion on acid basis was: 94.7 mol %

The selectivity to vinylester was: 99.1% wt

EXAMPLE 2

The experiment of Example 1 was repeated, using the same conditions with the exception of the temperature which was now: 300° C.

The conversion on acid basis was: 98.0 mol %.

The selectivity to vinylester was: 99.2% wt.

EXAMPLE 3

The experiment of Example 1 was repeated, using the same conditions with the exceptions of the temperature which was now 249° C., and the WHSV which was now 0.815 and 0.565 g/g/h for the acid and the acetylene, respectively. Moreover the zinc content of the catalyst was 20% wt.

The conversion on acid basis was: 96.6 mol %.

The selectivity to vinylester was: 99.0% wt.

EXAMPLE 4

The experiment of Example 3 was repeated, using the same conditions with the exception of the temperature which was now: 300° C.

The conversion on acid basis was: 98.4 mol %.

The selectivity to vinylester was: 99.0% wt.

We claim:

1. A process for making branched vinylesters, comprising:
reacting a gaseous mixture in the presence of a catalyst composition comprising zinc and an alumina carrier, wherein the gaseous mixture comprises acetylene and at least one branched carboxylic acid selected from the group consisting of secondary carboxylic acids, tertiary carboxylic acids, and combinations thereof having the following formula:

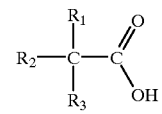

wherein $R_1$ is hydrogen or an alkyl group, and $R_2$ and $R_3$ are alkyl groups, wherein a total number of carbon atoms of $R_1+R_2+R_3$ is from 3 to 18, wherein the acetylene and the branched carboxylic acid have a molar ratio from about 0.5 to about 10, and wherein a weight hourly space velocity of the branched carboxylic acid is from about 0.2 to about 10 grams of branched carboxylic acid per gram of catalyst per hour.

2. The process of claim 1 wherein the molar ratio is from about 1 to about 5.

3. The process of claim 1 wherein the reaction occurs at an elevated temperature from about 150 to about 400° C.

4. The process of claim 1 wherein the reaction has a pressure from about 0.1 to about 5 bars.

5. The process of claim 2 wherein the weight hourly space velocity of the branched carboxylic acid is from about 0.5 to about 5 grams of branched carboxylic acid per gram of catalyst per hour.

6. The process of claim 1 wherein the catalyst comprises 0.1 to 30% by weight of zinc.

7. The process of claim 6 wherein the catalyst comprises 1 to 20% by weight of zinc.

8. The process of claim 1 wherein the catalyst is prepared by impregnating the alumina carrier with a solution of at least one zinc salt and then drying the impregnated carrier.

9. The process of claim 8 wherein the zinc salt is zinc nitrate and/or zinc acetate.

10. The process of claim 8 wherein if the zinc salt is of an inorganic acid or of acetic acid, an aqueous solution of the zinc salt is used for the impregnation and if the zinc salt is an organic zinc salt, an alcohol or an ether solution of the zinc salt is used for the impregnation.

11. The process of claim 8 wherein an aqueous solution of the zinc salt is used for the impregnation.

12. The process of claim 8 wherein the zinc salt is zinc nitrate.

13. The process of claim 1 wherein the branched carboxylic acid comprises 2-ethyl-hexanoic acid.

14. A process for making branched vinylesters, comprising:
reacting a gaseous mixture in the presence of a catalyst composition comprising zinc and an alumina carrier, wherein the gaseous mixture comprises acetylene and at least one tertiary carboxylic acid having the following formula:

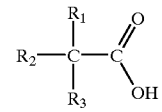

wherein $R_1$, $R_2$, and $R_3$ are alkyl groups, wherein a total number of carbon atoms of $R_1+R_2+R_3$ is from 3 to 18, wherein the acetylene and the at least one tertiary carboxylic acid have a molar ratio from about 1 to about 5, and wherein a weight hourly space velocity of the carboxylic acid is from about 0.5 to about 5 grams of carboxylic acid per gram of catalyst per hour.

15. The process of claim 14 wherein the catalyst comprises 0.1 to 30% by weight of zinc and is prepared by impregnating the alumina carrier with a solution of at least one zinc salt and then drying the impregnated carrier.

16. The process of claim 15 wherein the zinc salt is zinc nitrate, zinc acetate, or combinations thereof.

* * * * *